United States Patent [19]
Taylor et al.

[11] Patent Number: 5,676,653
[45] Date of Patent: Oct. 14, 1997

[54] KINK-RESISTANT STEERABLE CATHETER ASSEMBLY

[75] Inventors: Kevin Taylor, Reading; Philip F. Latzgo, Etters; Timothy J. Lenihan, Reading, all of Pa.

[73] Assignee: Arrow International Investment Corp., Wilmington, Del.

[21] Appl. No.: 619,912

[22] Filed: Mar. 20, 1996

Related U.S. Application Data

[63] Continuation-in-part of Ser. No. 534,345, Sep. 27, 1995, which is a continuation-in-part of Ser. No. 495,356, Jun. 27, 1995, abandoned.

[51] Int. Cl.$^6$ .................................................. A61M 37/00
[52] U.S. Cl. .................................................. 604/95; 604/280
[58] Field of Search ..................... 604/95, 22, 101–103, 604/264, 280; 606/33, 41

[56] References Cited

U.S. PATENT DOCUMENTS 5,364,352  11/1994  Cimino et al. ........................ 604/95

Primary Examiner—John D. Yasko
Attorney, Agent, or Firm—Amster Rothstein & Ebenstein

[57] ABSTRACT

A kink-resistant steerable catheter assembly suitable for microwave ablation includes a handle, a catheter and a steering control. The catheter has (a) a flexible, torque-transmitting and axially incompressible proximal or body portion terminating in a proximal end attached to the handle, and (b) a flexible and axially compressible distal or tip portion terminating in a distal end. A coaxial cable is disposed in and extends through a large aperture in the catheter proximal portion, and a coaxial cable extension is generally centrally disposed in, substantially fills, and snugly extends through a large lumen in the catheter distal portion to reduce kinking. The control is disposed in and actuatable from the handle, for placing tension on one of a pair of steering wires while relaxing tension on the other of the pair of steering wires, thereby to bend the distal end of the coaxial cable extension toward the tensed one of the steering wires.

22 Claims, 6 Drawing Sheets

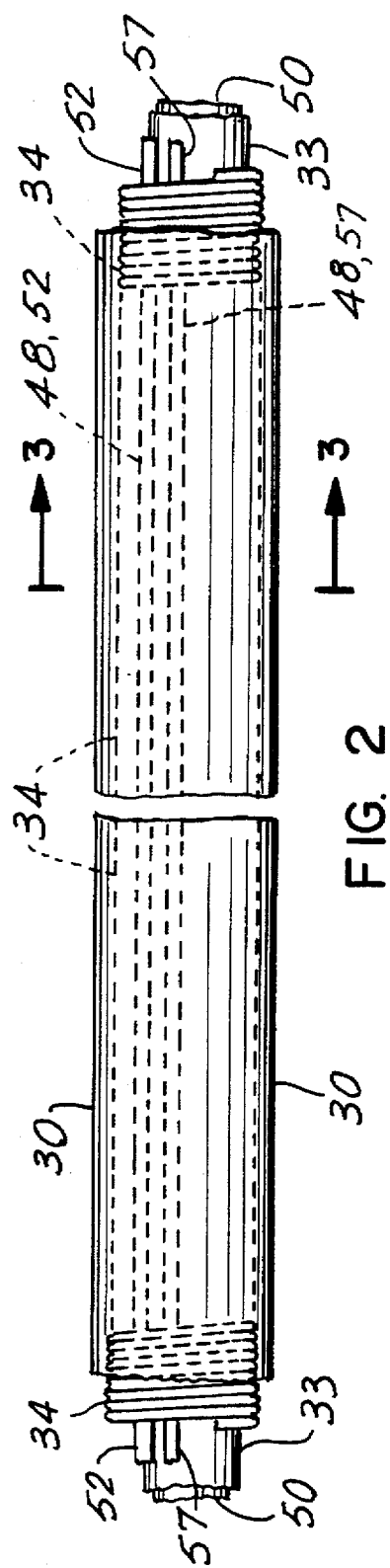
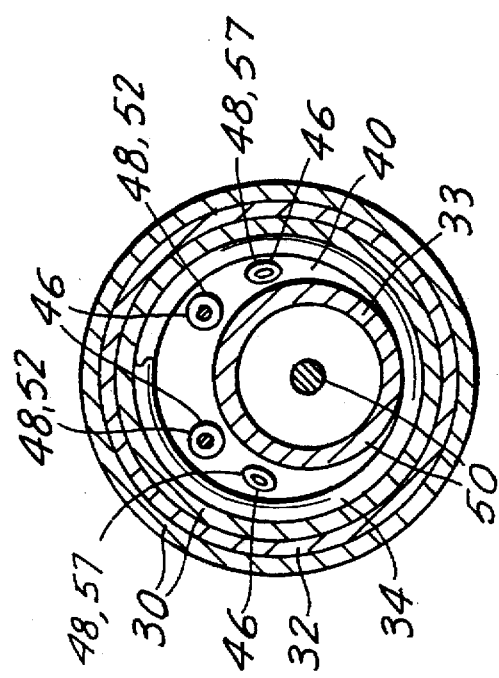
FIG. 2
FIG. 3

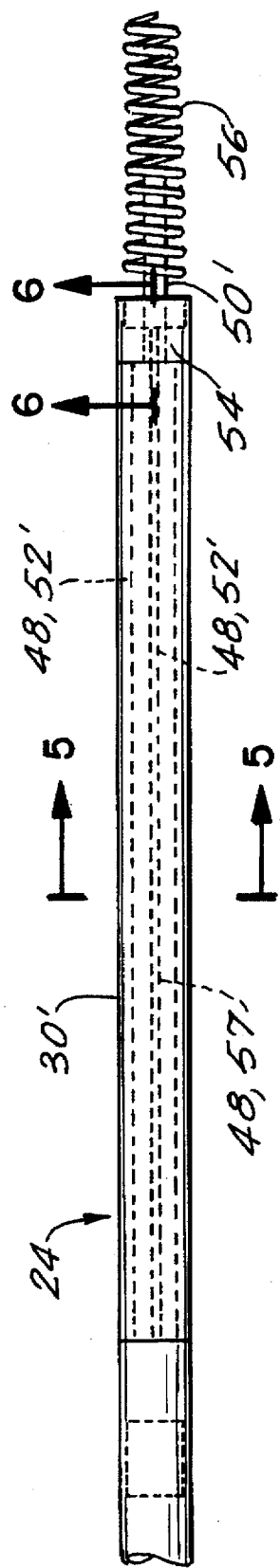
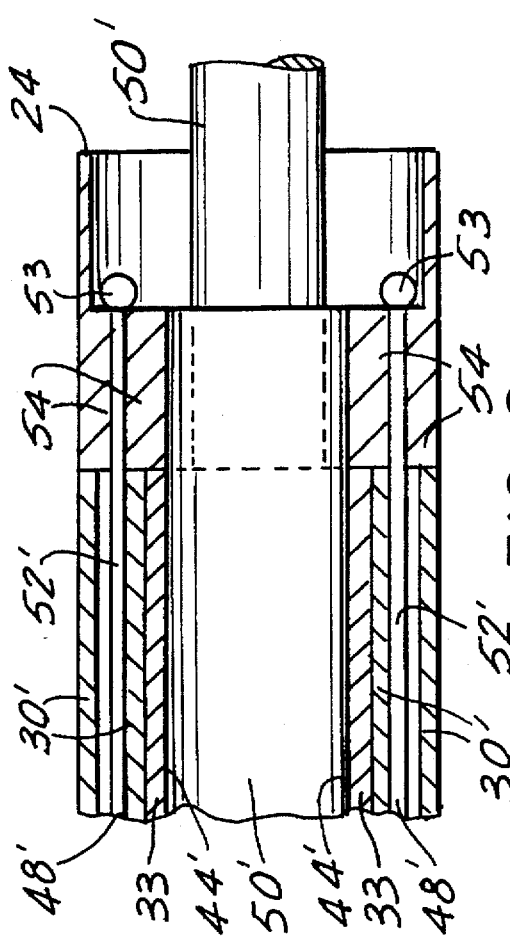
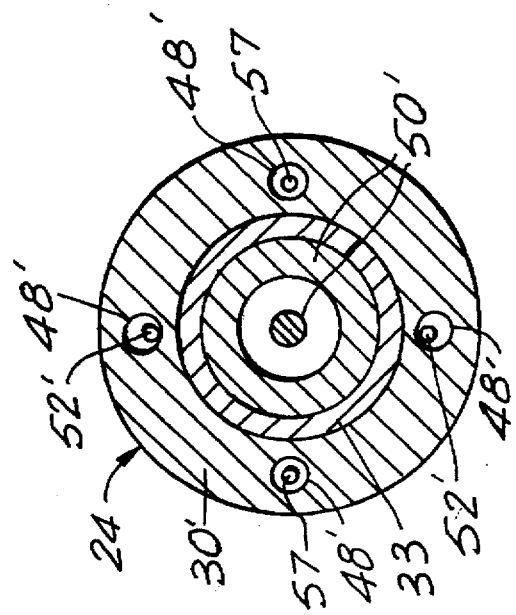

KINK-RESISTANT STEERABLE CATHETER ASSEMBLY

CROSS-REFERENCE TO RELATED APPLICATIONS

The present application is a continuation-in-part of U.S. patent application Ser. No. 08/534,345, filed Sep. 27, 1995; itself a continuation-in-part of U.S. patent application Ser. No. 08/495,356, filed Jun. 27, 1995, now abandoned.

BACKGROUND OF THE INVENTION

The present invention relates to a steerable catheter assembly and, more particularly, to such a catheter assembly which is kink-resistant and suitable for use in microwave ablation.

In many medical procedures, it is necessary to position a catheter at a location within a patient's body. A typical emplacement for the distal end of a catheter might be within a ventricle of the heart, by way of the femoral artery. In so passing a catheter through the femoral artery, it is necessary to avoid obstructions, vessel junctions, and the like, and to make sharp turns to position the distal end of the catheter within the ventricle. Other medical procedures involve similar difficulties in placing a catheter.

Thus, steering mechanisms for catheters and other devices have been developed wherein the distal end of the device can be manipulated at will from a location outside the patient's body or outside the apparatus in which the device is placed. Catheter assemblies with the known steering mechanisms therein have not proven to be entirely satisfactory in use. For example, kinking of the catheter within the patient is a common problem, especially at the distal end of the catheter.

Typically, the physician is able to employ a conventional steerable catheter assembly which enables a soft distal region of a tubular shaft to deflect without altering the shape or stiffness of the proximal region of the shaft. Many of these steerable catheter assemblies utilize a pull wire system wherein a flat metal lead spring runs down the center of the soft distal portion of the tube and has a pair of pull wires attached to the very end thereof. By pulling on one pull wire, while the other pull wire is relaxed, the tip or front soft portion deflects. The centrally located metal lead spring acts as a biasing means to bias the catheter assembly to return the deflected tip to its original position and also to restrict the steering motion to one plane (that is, to opposite directions). See, for example, U.S. Pat. No. 5,336,182 and PCT International Application Publication No. WO 91/11213.

Another method uses a multi-lumen tube for the distal portion, the multi-lumen tube consisting of a central lumen with multiple off-center smaller lumens. The pull wires extend through the proximal section of the shaft and are diverted off-center into the off-center lumens at the beginning of the distal section. The pull wires are attached to the end of the distal section such that, when one wire is pulled and the other released, the tip of the tube is deflected in the direction of the pulled pull wire. A preferred method for tensioning pull wires utilizes a rotating, contoured pull wheel with two attached pull wires to deflect the distal tip in two directions. See, for example, U.S. Pat. No. 04,960,134, U.S. Pat. No. 5,318,525, and U.S. Pat. No. 5,328,467.

For the catheter steering to be effective, only the distal portion of the tube should deflect. Thus, the proximal portion of the catheter must be incompressible along its axial direction when a tension force is applied to the pull wires. This will keep the proximal portion of the catheter from bending and allow only the soft distal portion to bend and deflect. However, the catheter assembly must also remain flexible itself so it can be placed through tortuous blood vessels.

In addition to being steerable in a lateral direction, further positioning of known catheter assemblies is accomplished by rotating the catheter assembly as a whole about its longitudinal axis, typically by turning or twisting the proximal end of the catheter assembly. This exerts a torque along the length of the catheter assembly which is translated into a rotational motion at the distal end, thereby allowing a laterally deflected distal tip to be rotated.

A relatively new medical procedure requiring relatively exact placement of the catheter utilizes microwave (MW) energy to perform ablation rather than the conventional radio frequency (RF) energy. While RF energy may be transmitted along the length of a catheter by means of a relatively thin wire without damage to the other elements of the catheter, because of the nature of MW energy transmission and the continuing need to protect other elements of the catheter from the higher energies involved in MW transmission, it has been found necessary to utilize for MW transmission a coaxial cable rather than the thin wire used for RF transmission. For various reasons including the much greater diameter of a coaxial cable relative to a thin wire, the stiffness of the coaxial cable relative to a thin wire, and the limited space available within the interior of the catheter, the conventional steerable catheter assemblies do not lend themselves to microwave ablation.

Accordingly, it is an object of the present invention to provide a kink-resistant steerable catheter assembly.

Another object is to provide such a catheter assembly which employs a coaxial cable and is suitable for use in microwave ablation.

A further object is to provide such a catheter assembly which is relatively easy and inexpensive to manufacture, and easy to use and maintain.

SUMMARY OF THE INVENTION

It has now been found that the above and related objects of the present invention are obtained in a kink-resistant steerable catheter assembly comprising basically a handle, a catheter, and controller means. The catheter has (a) a flexible, torque-transmitting and axially incompressible proximal or body portion terminating in a proximal end attached to the handle, and (b) a flexible and axially compressible distal or tip portion terminating in a distal end. Controller means, disposed in and actuatable from the handle, place tension on one of a pair of steering wires while relaxing tension on the other of the steering wires, thereby to bend the distal end of the coaxial cable toward the tensed one of the steering wires.

More particularly, the proximal portion of the catheter includes an outer extrusion formed of a thin-walled, resilient tubing, and torque-transmitting means for transmitting torque along the catheter proximal portion. An axially incompressible means precludes both compression and kinking of the catheter proximal portion. A large aperture extends through the catheter proximal portion. At least a pair of relatively small flexible shafts, each defining a relatively small lumen, extend through the large aperture. A coaxial cable is disposed in and extends through the large aperture, and each of a pair of steering wires extends through a respective one of the small lumens and has a proximal end exiting a proximal end of the respective small lumen and entering the handle.

More particularly, the distal portion of the catheter includes an outer extrusion extension formed of a resilient tubing, and stiffly resilient biasing means for biasing the catheter distal portion to its home orientation. A large lumen extends through the catheter distal portion defined by the stiff biasing means, and at least a pair of relatively small lumen extensions are defined by the outer extrusion extension. A coaxial cable extension is generally centrally disposed in, substantially filling, and snugly extending through the large lumen, and each of a pair of steering wire extensions extends through a respective one of the small lumen extensions and has a distal end attached to the cable extension adjacent a distal end thereof.

In a preferred embodiment of the catheter proximal portion, the torque-transmitting means is a metal braid encapsulated by the tubing, and the axially incompressible means is an axially incompressible wire coil snugly fitted within an inner surface of the outer extrusion. The large aperture is defined by the inner surface of the coil. The small lumens are off-center in the large aperture, and the small lumens may be disposed on the same, side of the large aperture. In a preferred embodiment of the catheter distal portion, the biasing means is a relatively stiff material snugly fitted within the outer extrusion extension.

The catheter assembly is designed, configured and dimensioned especially for use in microwave ablation.

To limit movement of the catheter distal portion to a simple plane, the outer extrusion extension is formed of stiffly resilient material for biasing the catheter distal portion to its home orientation and resisting kinking of the catheter distal portion. A central large, rectangular lumen extends through the catheter distal portion defined by the material, and at least a pair of relatively small, off-center lumen extensions extend through the catheter distal portion defined by the material. A coaxial cable extension extends through the large lumen, and a pair of steering wire extensions, at least one of the steering wire extensions being of rectangular cross-section, extend through respective ones of the small lumen extensions, and have a distal end attached to the coaxial cable extension adjacent a distal end thereof.

In a preferred embodiment, the small lumen extensions are diametrically off-center relative to the large lumen and on opposite sides thereof. Preferably each steering wire extensions is of rectangular cross-section. Alternatively, at least one, and optionally both, of the steering wire extensions are circular cross-section. The flexible distal or tip portion of the catheter is axially compressible.

The present invention also encompasses a kink-resistant steerable catheter assembly which includes axially incompressible means for defining a flex plane intermediate the pair of steering wire extensions and enabling the steering wire extensions to bend the distal end to either side of the flex plane.

In a preferred embodiment, the flex plane is intermediate the small lumen extensions and the steering wire extensions therein and enables the steering wire extensions to bend the large lumen and the coaxial cable extension therein to either side of the flex plane. The incompressible means may include a spaced parallel pair of axially incompressible rods. The rods may be circular or rectangular in cross-section. The incompressible means may alternatively be a single incompressible rod of rectangular cross-section defining the flex plane.

BRIEF DESCRIPTION OF THE DRAWINGS

The above and related objects, features and advantages of the present invention will be more fully understood by reference to the following detailed description of the presently preferred, albeit illustrative, embodiments of the present invention when taken in conjunction with the accompanying drawing wherein:

FIG. 2 is a side elevational view of the proximal or body portion of the catheter, with portions thereof broken away to reveal details of internal construction;

FIG. 3 is a sectional view of the body portion, to an enlarged scale, taken along the line 3—3 of FIG. 2;

FIG. 4 is a side elevational view of the distal or tip portion of the catheter;

FIGS. 5 and 6 are sectional views, to an enlarged scale, taken along the lines 5—5 and 6—6 of FIG. 4;

DETAILED DESCRIPTION OF THE PREFERRED EMBODIMENTS

Figure 1:
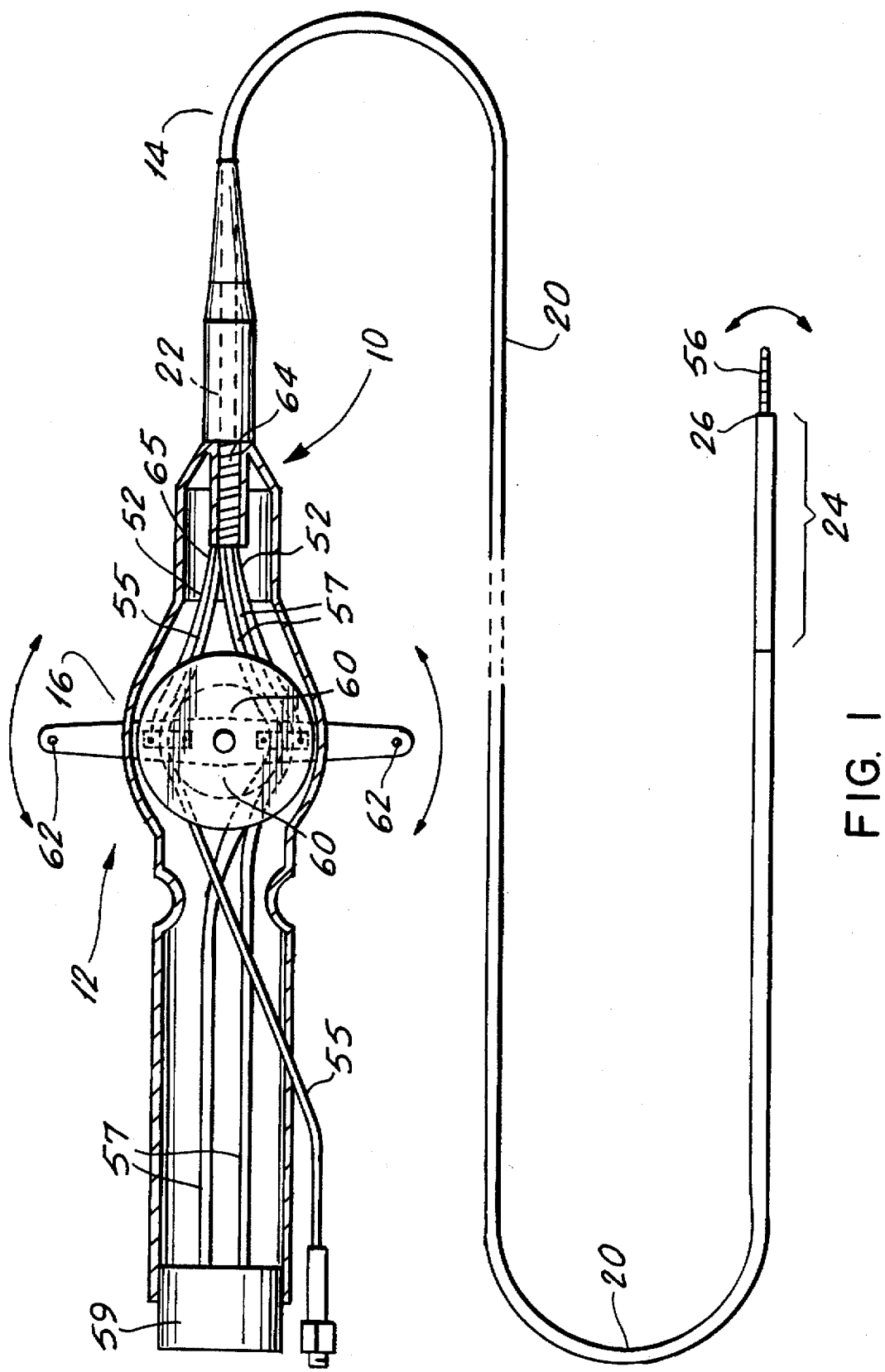
FIG. 1 is a top plan view of a kink-resistant steerable catheter assembly according to the present invention with portions of the handle removed to reveal details of internal construction.

Referring now to the drawing, and in particular to FIG. 1 thereof, therein illustrated is a kink-resistant steerable catheter assembly according to the present invention, generally designated by the reference numeral 10. The catheter assembly 10 is suitable for use in ablation therapy, and more particularly in microwave ablation therapy wherein the ablative energy is microwave energy. The catheter assembly 10 comprises a handle generally designated 12, a catheter generally designated 14, and controller means generally designated 16 and disposed in and actuatable from the handle 12. Proceeding from the proximal end to the distal end, the catheter 14 is itself divided into a flexible, torque-transmitting and axially incompressible proximal or body portion 20 terminating in a proximal end 22 attached to the handle 12, and a flexible and axially compressible distal or tip portion, generally designated 24, terminating in a distal end 26.

Turning now in greater detail to the proximal or body portion 20 of the catheter 14 and referring now to FIGS. 2 and 3 in particular, the catheter proximal portion 20 includes an outer extrusion 30 formed of a thin-walled, resilient tubing defining the outer surface of the catheter proximal portion 20. The extrusion 30 is formed of any of the biocompatible resilient plastics typically used in catheters, with polyimide and a polyurethan available under the tradename PEBAX (from Atochem of Glen Rock, N.J.) being preferred materials.

Disposed intermediate the inner and outer surfaces of the tubing 30 is a torque-transmitting means 32 for transmitting torque along the catheter proximal portion so that a surgeon can turn the catheter distal portion 24 and thus the distal end 26 by suitable manipulation of the handle 12 and thus the catheter proximal portion 20. A preferred torque-transmitting means 32 is a metal braid encapsulated by the tubing 30 intermediate the inner and outer surfaces of the tubing 30. A preferred metal braid 32 is formed of interleaved lengths of stainless steel and is disposed within the outer extrusion 30.

The catheter proximal portion 20 additionally includes axially incompressible means 34 for precluding both compression and kinking of the catheter proximal portion 20. A preferred incompressible means 34 is an axially incompressible wire coil snugly fitted within the outer extrusion 30, and more particularly within the inner surface of the outer extrusion 30. The coiled wire 34 may be manufactured by winding round wire around a mandrel so that the coils are adjacent and in contact with one another. The coil is then removed from the mandrel and allowed to relax. The inner diameter of the coiled wire should not exceed more than ten times the diameter of the stainless steel wire. Alternatively, flat wire may be used instead. A preferred wire is stainless steel. In any case, the wire coil is fed into the outer extrusion, the outer diameter of the coil being slightly less than the inner diameter of the outer extrusion 30. A tight fit must exist between the wire coil 34 and the outer extrusion 30 in order to maintain the integrity of the wire coil 34. If space were to exist intermediate the wire coil 34 and the outer extrusion 30, the wire coils could overlap under compressive forces and thereby degrade the steering performance. It will be appreciated that the wire coil 34 enables the catheter proximal portion 20 to be very incompressible, but yet flexible. End caps (not shown) are attached to the outer extrusion 30 at both ends to secure the same to the ends of coil 34, thereby to encapsulate and prevent extension of the wire coil 34.

The combined thickness of the outer extrusion 30 (which includes therein the metal braid 32) and the axially incompressible wire coil 34 is desirably kept to a minimum so that the outer diameter of the catheter meets a conventional size limitation (such as eight French size) and the outer diameter of a large aperture 40 within the combination is maximized, thereby to facilitate receipt therein and passage therethrough of the various other elements of the assembly, including the coaxial cable, wiring, etc.

The large aperture 40 extends through the catheter proximal portion 20 and is defined by the inner surface of the wire coil 34. The remaining components of the catheter proximal portion 20 are disposed within this large aperture 40 as follows:

A coaxial cable 50 is disposed in and extends through the large aperture 40. At least a pair of relatively small flexible shafts 46 (four being illustrated) extend through the large aperture 40, each defining a relatively small lumen 48. These shafts are preferably formed of PTFE (Teflon). Each of a pair of steering wires 52 (shown as a single line in FIG. 1) extends through a respective one of the small lumens 48. Each of the steering wires 52 has a proximal end exiting the proximal end of its respective small lumen 48, entering the handle 12, and being functionally connected to the controller means 16 therewithin. As will be seen shortly, the steering wires 52 or extensions thereof are functionally associated with the coaxial cable 50 to enable steering thereof (and of the catheter distal portion 24) in two directions, with the natural strong resiliency of the coaxial cable 50 tending to return the cable (and the catheter distal portion) to an original unbent and unstressed "home" position.

It will be appreciated by those skilled in the catheter art that the available space within the large aperture 40 has been exaggerated for expository purposes and typically there is little room to spare. Within the catheter proximal portion 20, the large coaxial cable 50 and the relatively small flexible shafts 46 (two of which include the steering wires 52) may be disposed in any compact orientation fitting within the large aperture 40, and it is not necessary at this point that the steering wires 52 be disposed on opposite sides of the coaxial cable 50. The large coaxial cable 50 and small lumens 48 are typically off-center in the large aperture 40, the small lumens 48 typically being disposed on the same side of the large coaxial cable 50 within the large aperture 40. The small shafts 46 (with their small lumens 48) not occupied by the steering wires 52 may be used for thermocouples or additional electrical leads 57 extending to the distal end 26 of the catheter 14 and being electrically connected at the other end to a socket 59 in the handle 12.

Turning now in greater detail to the catheter distal or tip portion 24, and referring now to FIGS. 4–6 in particular, the catheter distal portion 24 includes an outer extrusion extension 30' formed of a thin-walled, resilient tubing. The outer extrusion extension 30' is preferably formed of a urethane/nylon blend of Durometer 40D available under the trade name PEBAX from Atochem of Glen Rock, N.J., although different materials may be used if desired. A stiffly resilient biasing means 33 is fitted within the inner surface of the outer extrusion extension 30' for biasing the catheter distal portion 24 to its home orientation. The preferred material for the stiffly resilient biasing means 33 is a polyimide, although other stiffly resilient biasing materials may be employed. The stiffly resilient biasing means 33 cooperates with the coaxial cable extension 50' to be described hereinbelow in biasing the catheter distal portion 24 to its home or unstressed orientation.

A large lumen 44 extends through the catheter distal portion 24 within the inner surface of the biasing means 33, and at least a pair of relatively small lumen extensions 48' (four being shown) extend through the outer extrusion extension 30' and, more particularly, intermediate the inner and outer surfaces of the outer extrusion extension 30'.

A coaxial cable extension 50' is generally centrally disposed in, substantially fills, and snugly extends through the large lumen 44. By way of example, the large lumen 44 may have an internal diameter of 0.055 inch, and the coaxial cable extension 50' may have an external diameter of 0.052–0.054 inch. The snug match between the outer diameter of the coaxial cable extension 50' and the inner diameter of the large lumen 44 precludes any kinking of the coaxial cable extension 50' and therefore precludes any kinking of the catheter distal portion 24. A pair of steering wire extensions 52' extend through a respective pair of diametrically-opposed, off-center small lumen extensions 48'. Each steering wire extension 52' has a distal end functionally attached to an opposite side of the distal end of the coaxial cable extension 50'.

More particularly, a washer-like member or plastic ring 54 is disposed adjacent the distal end of the catheter tip 24 with suitable apertures for (five being shown) passage therethrough of the coaxial cable extension 50', the two steering wire extensions 52' (one steering wire extension 52' to either side of the coaxial cable extension 50') and two additional components such or a thermocouple lead, etc., from the two small lumen extensions 48'. The coaxial cable extension 50' extends through and is secured (e.g., by gluing or the like) to a large central aperture of the washer 54, and the steering wire extensions 52' extend through a pair of small off-center apertures and are either secured to the washer 54 adjacent diametrically-opposed ends thereof or are, as illustrated, provided with enlarged distal heads 53. The enlarged heads 53 at the end of the steering wire extensions 52' may be formed by silver solder beads, the beads preferably anchoring the distal tips of the wires 52' to the washer or plastic ring 54. Proximal pulling of a steering wire 52 will result in the corresponding steering wire extension 52' tipping the washer 54 in the direction of that steering wire extension 52', and thus the steering of the catheter distal portion 24 in that direction. When the tension on that steering wire 52, and thus that steering wire extension 52', is released, the catheter tip 24 will tend to resume its original or "home" orientation due to the combined action of the coaxial cable extension 50' and the biasing means 33.

The distal end 26 of the catheter assembly 10 is defined by an ablative electrode 56 in the form of a coiled wire electrically connected to an electrical source (not shown) by the coaxial cable extension 50', the coaxial cable 50, and the electrical lead 55 illustrated in FIG. 1.

Referring now to FIG. 1 in particular, the controller means 16 is disposed within and operable from outside the handle 12 for placing tension on one of the pair of steering wires 52 (and an associated extension 52') while relaxing tension on the other steering wire 52 (and its associated extension 52'), thereby to tilt the washer 54 and bend the distal end of the coaxial cable extension 50' towards the tensed one of the steering wire extensions 52'. Thus, a contoured pull wheel 60 has the two steering wires 52 fastened thereto on opposite sides of the wheel 60 such that, as one wire goes into tension, the other wire relaxes. The pull wheel 60 is designed to allow for maximum deflection of the distal tip of the catheter assembly 10 with minimal travel of the pull wheel 60. The contour of the pull wheel 60 is designed so that the steering wires 52 adjacent thereto are not exposed to any sharp angles which might cause the steering wires 52 to fatigue during operation or to break under tension. Indeed, it is contoured to allow the steering wires 52 to relax, when not in use, to avoid fatigue failure of the wires. The housing of the handle 12 encases all of the mechanical elements of the controller means 16 except for a pair of manually accessible grips 62 secured to the pull wheel 60 to effect limited rotation thereof.

In order to achieve effective steering, the steering wires 52 (and their extensions 52') must be adjusted initially to an appropriate tension. To this end, a screw 64 is provided for varying the spacing between the proximal end of the catheter 14 and the distal of the handle 12 so that the effective length of the catheter 14 (and indeed the entire catheter assembly 10) may be increased to place additional tension on the steering wires 52 or reduced to relax the tension thereon.

As will be appreciated by those skilled in the art, means must be provided for the steering wires 52 to accumulate in the handle 12. If the wires 52 have no space 65 in which to compress, they will fail at the point of bending after only minimal movements of the pull wheel 60 due to fatigue fracture. Inasmuch as handle-mounted controller means of this type are well known in the art (see, for example, PCT Publication WO91/11213 and U.S. Pat. No. 5,328,467), further details thereof need not be provided herein.

The design of the present invention enables a maximum amount of central material (i.e., coaxial cable) to be both disposed in the catheter and steered laterally, without the use of any flexible metal within the catheter distal portion for biasing the same. Indeed, the presence of the massive coaxial cable extension within the catheter distal end precludes the disposition of any flexible metal therein in order to aid in steering.

To summarize, the present invention provides a kink-resistant steerable catheter assembly, the assembly employing a coaxial cable and thus being suitable for use in microwave ablation. The catheter assembly is relatively easy and inexpensive to manufacture and easy to use and maintain.

It will be appreciated by those skilled in the steerable catheter art that it is highly desirable for the catheter motion transverse to its longitudinal axis to be limited at the distal end to a single plane. Thus it is intended that the steering wires 52, 52' be diametrically opposed (that is, on opposite sides of the coaxial cable 50, 50') so as to be able to flex the coaxial cable in either one direction or the 180° opposite direction. It is therefore considered detrimental to operation of the catheter when either the steering wires or the resilient biasing means of the distal portion result in a movement of the catheter distal portion which is not within the intended plane.

Figure 9:
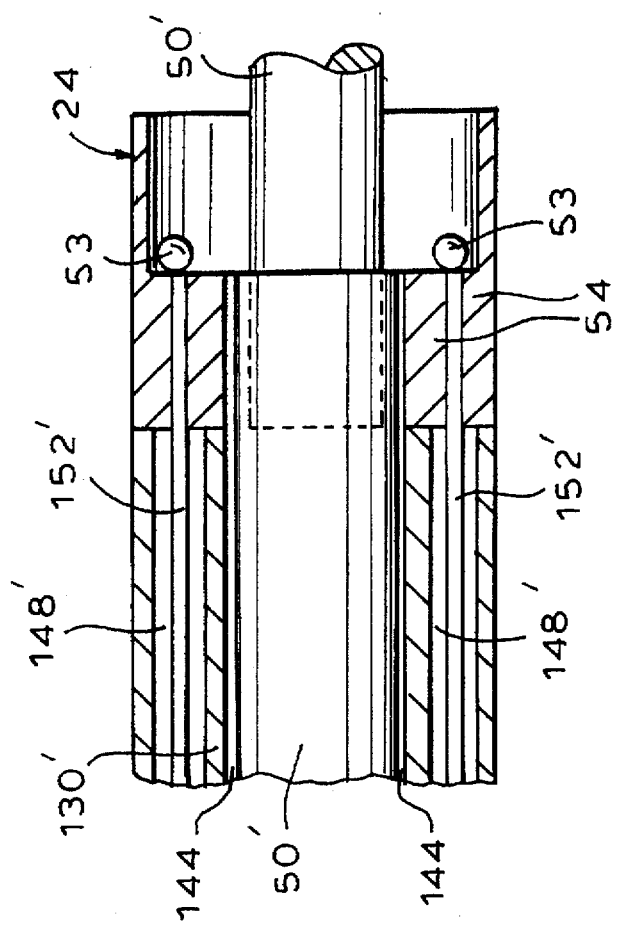
FIGS. 7, 8 and 9 are views similar to FIGS. 4, 5 and 6, but taken on an assembly with improved steering capabilities.
Figure 8:
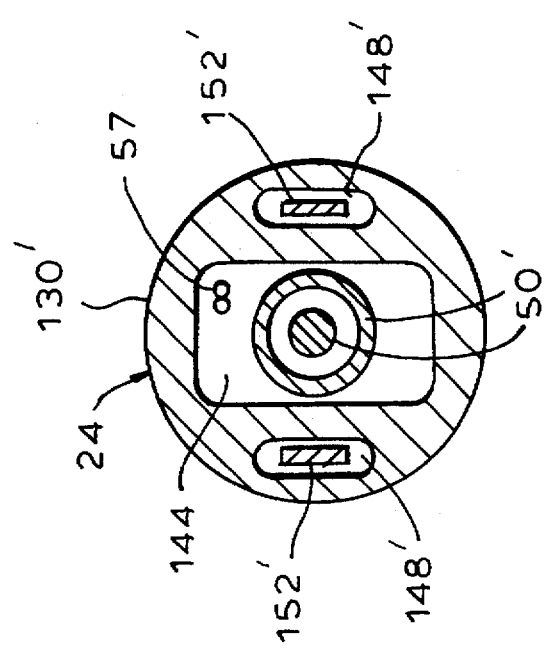
Figure 7:
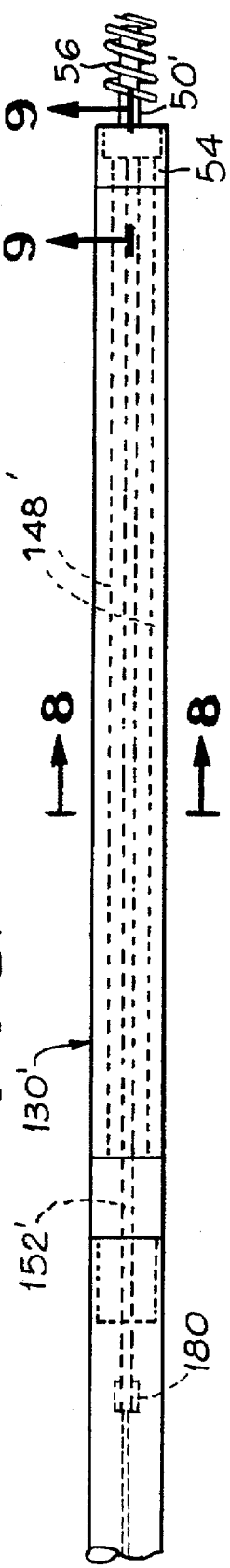

It has now been found that the stiffly resilient biasing means 33 for biasing the catheter distal portion 24 to its home orientation and resisting kinking thereof frequently returns the catheter distal portion 24 to an orientation not within the intended plane of its operation. Referring now to FIGS. 7-9 in particular, this problem is at least partially overcome if the stiffly resilient biasing means 33 is eliminated. Notwithstanding the improvement in operation of the device effected by this modification, however, return of the coaxial cable extension 50' to its home orientation remains problematic.

Referring now still to FIGS. 7-9, therein illustrated is an improved embodiment of the present invention which achieves a positive return of the coaxial cable extension 50' to its home orientation as well as effective restriction of the movement of the coaxial cable extension 50' to a single plane. As noted above, the modified outer extrusion 130' is preferably used without a stiffly resilient biasing means 33. The modified outer extrusion extension 130' defines a central rectangular lumen 44 and two additional off-center rectangular lumens 148' which are of greatly smaller dimensions than the central lumen 144 and placed close to the outside of the catheter diameter, with the long edges of both the central and off-center rectangular lumens 144, 148' being parallel to one another. The central rectangular lumen 144 and two off-center rectangular lumens 148' have rounded corners to minimize abrasion of or by the elements within the lumens.

Disposed within each of the off-center rectangular lumens 148' is a stainless steel steering wire extension 152' of flat cross section. The use of flat steering wire extensions permits the distal tip to deflect in one plane without allowing the coaxial cable 50, 50' to dictate the path of deflection. The flat wire 152' is preferably from 0.006 inch×0.020 inch to 0.007×0.030 inch. The flat steering wire extensions 152' are connected to the round steering wires 52 of the catheter proximal portion 20 by brazing or the like. The brazing joint of the two geometrically dissimilar wires 52, 152' is located at 180 in the incompressible catheter body 20 adjacent the proximal end thereof. The long axis of each flat wire extension 152' is aligned with the long axis of its respective off-center rectangular lumen 148'. Eventually, as illustrated in FIG. 9, the distal ends of flat wire extensions 152' are secured to the washer 54 for deflecting the catheter distal portion 24. While the flat wire extensions 152' are illustrated as substantially smaller in both cross-sectional dimensions than the off-center lumens 148', it will be appreciated that a snugger fit is also possible. The larger width aspect (0.020 inch–0.007 inch), compared to the smaller thickness aspect (0.006 inch–0.007 inch), allows each of flat wire extensions 152' to bend around its lateral axis (which is perpendicular to the plane in which the catheter distal tip needs to deflect)

and prevents bending around its longitudinal axis. Similarly, while the coaxial cable extension 50' is illustrated as substantially smaller in both cross-sectional dimensions than central rectangular lumen 44, it will be appreciated that a snugger fit is also possible as long as it enables the lumen 144 to house the coaxial cable extension 50' as well as any required electrical leads 57, which may include, for example, therecouple leads, pacing leads, etc.

With some loss of effectiveness relative to the use of two flat steering wire extensions 152', a hybrid catheter with one flat steering wire extension and one round steering wire extension may be used.

Each of the catheter embodiments described hereinabove utilizes a compressible distal or tip portion which may be manipulated by steering wires to deflect a solid inner member (i.e., a coaxial cable) in a single plane of motion, However, the durability and longevity of such catheters may not always be sufficient. The repeated compression of the distal portion during the deflection of the solid inner member (that is, the coaxial cable) may contribute to the shortening of the longevity of the distal portion. Additionally, the repeated compression of the distal portion directs a high level of compressive forces towards the incompressible proximal portion of the catheter with resultant adverse effects on the durability and longevity of the proximal portion. Accordingly, the present invention is also directed to a variant of the foregoing embodiments wherein the distal portion is longitudinally incompressible.

More particularly, as seen in FIGS. 10–13, the incompressibility of the distal portion is achieved by the incorporation therein of longitudinally incompressible support means, generally designated 200, for defining a flex plane designated 202 (illustrated in phantom line as coming out of the plane of the paper) intermediate the two steering wire extensions 152' and enabling the steering wire extensions 152' to bend the distal end to either side of the flex plane 202. The disposition of the flex plane 202 intermediate the small lumen extensions 148' and the steering wire extensions 152' therein enables the steering wire extensions to bend the large lumen 144 and the coaxial cable extension 50' therein to either side of the flex plane 202.

Figure 10:
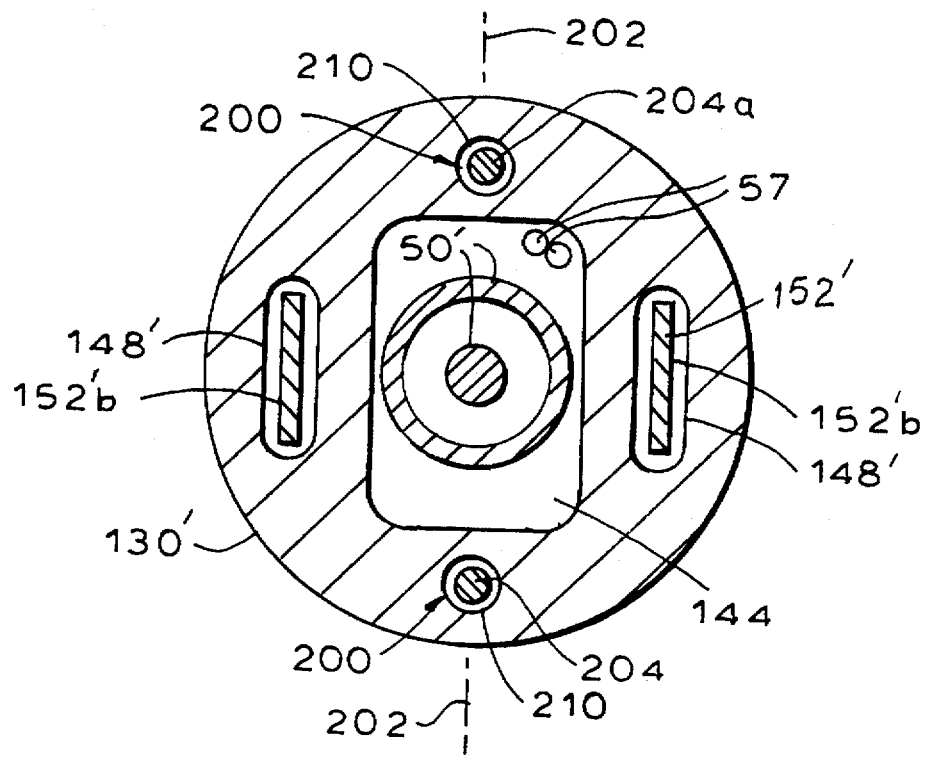
FIG. 10 is a view similar to FIG. 8 of a variant using circular incompressible support rods.
Figure 11:
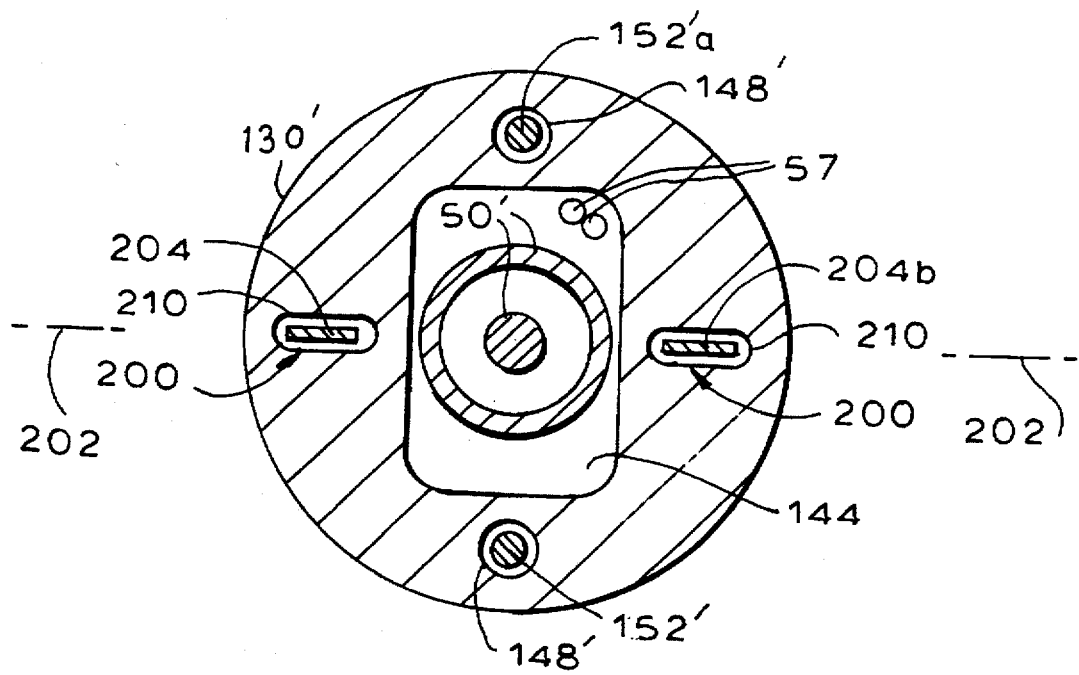
FIG. 11 is a view similar to FIG. 8 of a variant using flat rectangular incompressible support rods.
Figure 12:
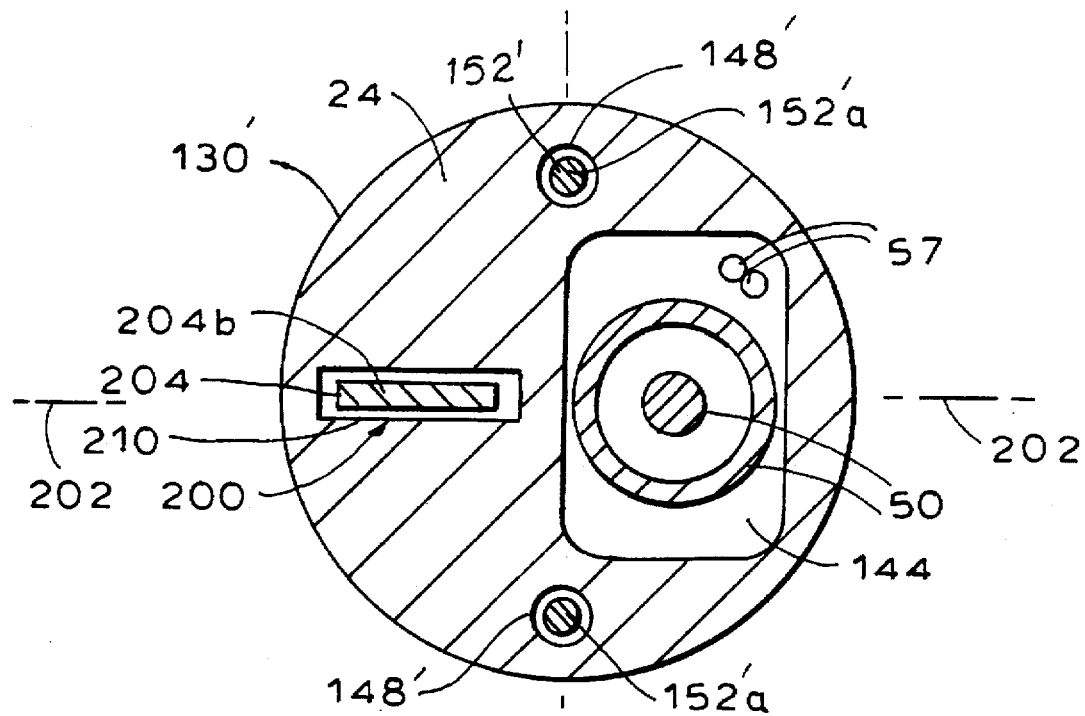
FIG. 12 is a view similar to FIG. 8 of a variant using a single flat rectangular incompressible support rod.

Typically, the incompressible support means 200 includes a spaced parallel pair of incompressible support rods 204. The incompressible support rods 204 may be circular in cross-section (rods 204a as illustrated in FIG. 10) or flat rectangular in cross-section like a ribbon (rods 204b as illustrated in FIG. 11). Alternatively, the incompressible support means 200 may be a single incompressible support rod 204b of flat rectangular cross-section (as illustrated in FIG. 12). It will be appreciated by those skilled in the art that, where there are two incompressible support rods cooperatively defining therebetween a flex plane, both incompressible support rods 204 may be either circular or flat rectangular in cross-section and, indeed, one may be circular and the other may be flat rectangular. On the other hand, where there is but a single incompressible support rod 204, that incompressible support rod 204b must be flat rectangular in cross-section in order to define by itself the flex plane. Where there are a pair of flat rectangular support rods 204b defining the flex plane 202, the rods 204b are in end-to-end alignment.

Just as the incompressible support rods 204 may be either flat rectangular or circular in cross-section, the steering wire extensions 152' (and the small lumen extensions 148' thereabout) may be either circular in cross-section (wire extension 152'a as in FIG. 11) or flat rectangular (wire extensions 152'b as in FIG. 10). The use of a round steering wire extension 152'a or incompressible support rod 204a decreases the overall stiffness of the distal portion because it decreases the total cross-sectional area of the steering wire extension or incompressible support rod, thereby allowing for easier advancement of the catheter across areas where flexibility is necessary (such as the aortic valve).

Referring now to FIG. 10, therein illustrated is a catheter similar to that illustrated in FIG. 8, but also having in the distal portion a spaced parallel pair of incompressible support rods 204a of circular cross-section, one to either side of the large lumen extension 144, for defining a flex plane 202. It will be appreciated that the flex plane 202 extends intermediate the steering wire extensions 152'b and enable the steering wire extensions 152'b to bend the distal end to either side of the flex plane 202.

Referring now to FIG. 11, therein illustrated is a catheter also similar to that illustrated in FIG. 8 but also having in the distal portion a spaced parallel pair of incompressible support rods 204b of flat rectangular cross-section, one to either side of the large lumen extension 144, for defining a flex plane 202 intermediate the circular steering wire extensions 152'a.

Referring now to FIG. 12, therein illustrated is a catheter also similar to that illustrated in FIG. 8 but also having in the distal portion incompressible means 200 for defining a flex plane 202 intermediate the steering wire extensions 152' and enabling the steering wire extensions 152' to bend the distal end to either side of the flex plane 202. The incompressible means 200 in this embodiment is a single incompressible support rod 204b of flat rectangular cross-section so as to enable flex of the distal portion towards either of the circular steering wire extensions 152'a. In this instance, the incompressible support rod 204b must be rectangular in cross-section, and not simply circular in cross-section.

Figure 13:
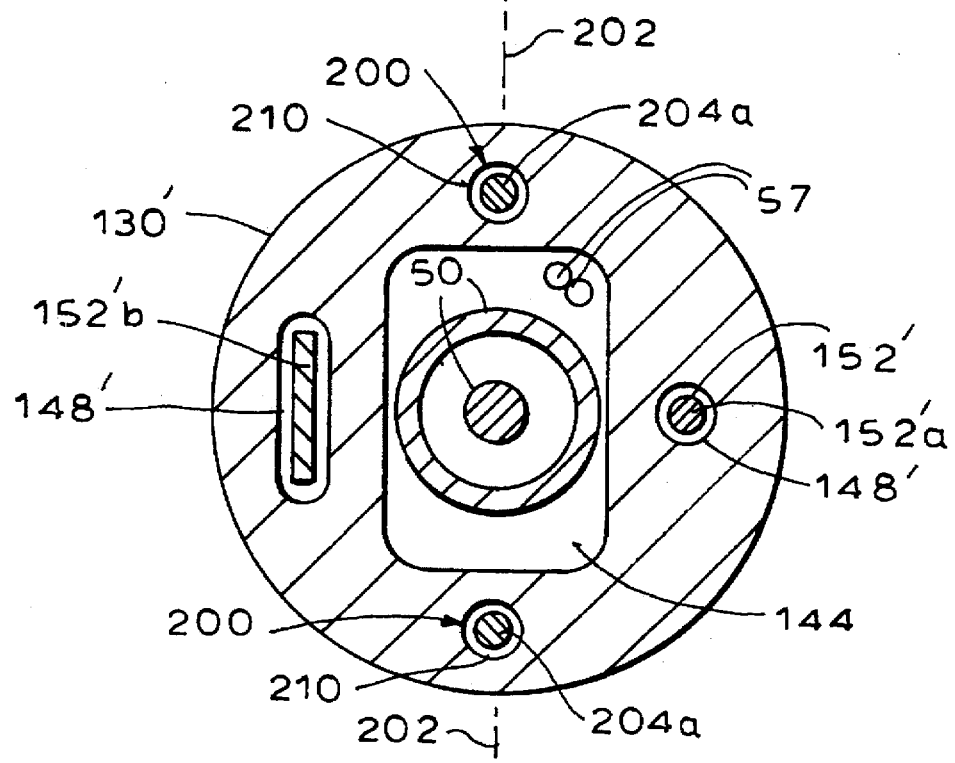
FIG. 13 is a view similar to FIG. 8 of a variant using circular incompressible support rods, one flat rectangular steering wire extension, and one round steering wire extension.

Referring now to FIG. 13, therein illustrated is a catheter wherein one steering wire extension 152'b is flat rectangular in cross-section and the other steering wire extension 152'a is round in cross-section, the two incompressible support rods 204a being circular in cross-section.

In each of the embodiments of FIGS. 10–13, the small lumens 148' for the flat rectangular steering wire extensions 152'b are rectangular in cross-section, and those for the circular steering wire extensions 152'a are circular in cross-section.

Typically, although not necessarily, the plane 202 defined by the incompressible support rod or rods 204 will extend through the coaxial cable extension 50'. To facilitate the appropriate placement of the incompressible support rods 204, the small lumen extensions 148' and the contents 152' thereof may be relocated within the extrusion extension 24.

While the steering wire extensions 152' are necessarily disposed in the small lumens 148' to enable movement of the extensions within the lumens, the incompressible support rods 204 may either be disposed in appropriate small lumens 210 (whether circular or flat rectangular in cross-section) or the catheter may be formed with the rods 204 in situ. The ability to form the catheter with the incompressible support rods in situ enables manufacturing economies. The movement of the support rods 204 relative to the contiguous plastic of the catheter is so nominal than the contiguous plastic does not hinder the nominal movement of the support rods 204 relative thereto, even in the absence of a surrounding small lumen.

The incompressible support rods 204 are preferably constructed of non-malleable materials which in the finished shape are both flexible and axially incompressible. Preferred materials are those available under the trade name NITINOL, a Ni/Ti alloy available from Raychem of Menlo Park, Calif.; 304 V STAINLESS STEEL, a vacuum heat-treated stainless steel available from Fort Wayne Metals of Fort Wayne, Ind.; and selected plastics; etc. The incompressible support rods are inserted into appropriate lumens therefore and then secured at their distal and proximal ends by RF (radio frequency) or like joining with an adjacent material. The incompressible support rods restrict the distal portion from absorbing the compressive forces generated by the steering wire extensions, thereby improving the durability of the distal portion.

To summarize, the presence of the incompressible support means improves the durability and longevity of the catheter while still permitting the distal portion to deflect in a single plane. Further, the presence of the incompressible support means enables the Durometer hardness of the extrusion to be decreased (for example, from about 40D units to about 35D units), thereby lowering the force which must be exerted in order to deflect the distal portion. Accordingly, this feature not only enhances the durability of the catheter, but also its ease of use.

Now that the preferred embodiments of the present invention have been shown and described in detail, various modifications and improvements thereon will become readily apparent to those skilled in the art. Accordingly, the spirit and scope of the present invention is to be construed broadly, and limited only by the appended claims, and not by the foregoing specification.

We claim:

1. A kink-resistant steerable catheter assembly comprising:
   (A) a handle;
   (B) a catheter having (a) a flexible, torque-transmitting and axially incompressible proximal or body portion terminating in a proximal end attached to said handle, and (b) a flexible and axially compressible distal or tip portion terminating in a distal end;
      (a) said proximal portion of said catheter including:
         (i) an outer extrusion formed of a thin-walled, resilient tubing,
         (ii) torque-transmitting means for transmitting torque along said catheter proximal portion,
         (iii) axially incompressible means for precluding both compression and kinking of said catheter proximal portion,
         (iv) a large aperture extending through said catheter proximal portion,
         (v) at least a pair of relatively small flexible shafts, each said small shaft extending through said large aperture and defining a relatively small lumen,
         (vi) a coaxial cable disposed in and extending through said large aperture, and
         (vii) a pair of steering wires, each of said steering wires extending through a respective one of said small lumens, and having a proximal end exiting a proximal end of said respective small lumen and entering said handle; and
      (b) said distal portion of said catheter including:
         (i) an outer extrusion extension formed of a resilient tubing,
         (ii) stiffly resilient biasing means for biasing said catheter distal portion to its home orientation and resisting kinking of said catheter distal portion,
         (iii) a large lumen through said catheter distal portion defined by said stiff biasing means,
         (iv) at least a pair of relatively small lumen extensions defined by said outer extrusion extension,
         (v) a coaxial cable extension generally centrally disposed in, substantially filling, and snugly extending through said large lumen, and
         (vi) a pair of steering wire extensions, each of said steering wire extensions extending through a respective one of said small lumen extensions, and having a distal end attached to said cable extension adjacent a distal end thereof; and
   (C) controller means, disposed in and actuatable from said handle, for placing tension on one of said steering wires while relaxing tension on the other of said steering wires, thereby to bend said distal end of said coaxial cable toward said tensed one of said steering wires.

2. The catheter assembly of claim 1 wherein said torque-transmitting means is a metal braid encapsulated by said tubing.

3. The catheter assembly of claim 1 wherein said axially incompressible means is an axially incompressible wire coil snugly fitted within an inner surface of said outer extrusion.

4. The catheter assembly of claim 3 wherein said large aperture is defined by said coil.

5. The catheter assembly of claim 1 wherein said small lumens are off-center in said large aperture.

6. The catheter assembly of claim 1 wherein small lumens are disposed on the same side of in said large aperture.

7. The catheter assembly of claim 1 wherein said biasing means is a relatively stiff material snugly fitted within said outer extrusion extension.

8. A kink-resistant steerable catheter assembly for use in microwave ablation, comprising:
   (A) a handle;
   (B) a catheter having (a) a flexible, torque-transmitting and axially incompressible proximal or body portion terminating in a proximal end attached to said handle, and (b) a flexible and axially compressible distal or tip portion terminating in a distal end;
      (a) said proximal portion of said catheter including:
         (i) an outer extrusion formed of a thin-walled, resilient tubing,
         (ii) torque-transmitting means for transmitting torque along said catheter proximal portion, including a metal braid encapsulated by said tubing,
         (iii) axially incompressible means for precluding both compression and kinking of said catheter proximal portion, including an axially incompressible wire coil snugly fitted within an inner surface of said outer extrusion,
         (iv) a large aperture extending through said catheter proximal portion,
         (v) at least a pair of relatively small flexible shafts, each said small shaft extending through said large aperture and defining a relatively small lumen, said small lumens being off-center in said large aperture, said small lumens being disposed on the same side of said large aperture,
         (vi) a coaxial cable disposed in and extending through said large aperture, and
         (vii) a pair of steering wires, each of said steering wires extending through a respective one of said small lumens, and having a proximal end exiting the proximal end of said respective small lumen and entering said handle; and
      (b) said distal portion of said catheter including:
         (i) an outer extrusion extension formed of a resilient tubing, (ii) stiffly resilient biasing means fitted within said outer extrusion extension for biasing said catheter distal portion to its home orientation, said stiffly resilient biasing means being defined by a relatively stiff material snugly fitted within said outer extrusion extension to resist kinking of said catheter distal portion, (iii) a large lumen through said catheter distal portion defined by said stiff material, (iv) at least a pair of relatively small lumen extensions defined by said outer extrusion extension, (v) a coaxial cable extension generally centrally disposed in, substantially filling, and snugly extending through said large lumen, and (vi) a pair of steering wire extensions, each of said steering wire extensions extending through a respective one of said small lumen extensions, and having a distal end attached to said coaxial cable extension adjacent a distal end thereof; and (C) controller means, disposed in and actuatable from said handle, for placing tension on one of said steering wires while relaxing tension on the other of said steering wires, thereby to bend said distal end of said coaxial cable toward said tensed one of said steering wires.

9. A kink-resistant steerable catheter assembly comprising:

(A) a handle;

(B) a catheter having (a) a flexible, torque-transmitting and axially incompressible proximal or body portion terminating in a proximal end attached to said handle, and (b) a flexible distal or tip portion terminating in a distal end;

(a) said proximal portion of said catheter including:

(i) an outer extrusion formed of a thin-walled, resilient tubing, (ii) torque-transmitting means for transmitting torque along said catheter proximal portion, (iii) axially incompressible means for precluding both compression and kinking of said catheter proximal portion, (iv) a large aperture extending through said catheter proximal portion, (v) at least a pair of relatively small flexible shafts, each said small shaft extending through said large aperture and defining a relatively small lumen, (vi) a coaxial cable disposed in and extending through said large aperture, and (vii) a pair of steering wires, each of said steering wires extending through a respective one of said small lumens, and having a proximal end and exiting a proximal end of said respective small lumen and entering said handle; and (b) said proximal portion of said catheter including:

(i) a solid extrusion extension formed of resilient material for biasing said catheter distal portion to its home orientation and resisting kinking of said catheter distal portion, (ii) a large, central lumen through said catheter distal portion defined by said extrusion extension, (iii) at least a pair of relatively small, off-center lumen extensions through said catheter distal portion defined by said extrusion extension, (iv) a coaxial cable extension extending through said large lumen, and (v) a pair of steering wire extensions, at least one of said steering wire extensions being of rectangular cross-section, said steering wire extensions extending through a respective one of said small lumen extensions and having a distal end attached to said cable extension adjacent a distal end thereof; and (C) controller means, disposed in and actuatable from said handle, for placing tension on one of said steering wires while relaxing tension on the other of said steering wires, thereby to bend said distal end of said coaxial cable toward said tensed one of said steering wires.

10. The catheter assembly of claim 9 wherein said small lumen extensions are diametrically off-center relative to said large lumen.

11. The catheter assembly of claim 9 wherein said small lumen extensions are disposed on opposite sides of said large lumen.

12. The catheter assembly of claim 9 wherein each of said steering wire extensions is of rectangular cross-section.

13. The catheter assembly of claim 9 wherein at least one of said steering wire extensions is of circular cross-section.

14. The catheter assembly of claim 9 wherein both of said steering wire extensions are of circular cross-section.

15. The catheter assembly of claim 9 wherein said flexible distal or tip portion of said catheter is axially compressible.

16. The catheter assembly of claim 9 wherein said flexible distal or tip portion of said catheter is axially incompressible.

17. A kink-resistant steerable catheter assembly comprising:

(A) a handle;

(B) a catheter having (a) a flexible, torque-transmitting and axially incompressible proximal or body portion terminating in a proximal end attached to said handle, and (b) a flexible distal or tip portion terminating in a distal end;

(a) said proximal portion of said catheter including:

(i) an outer extrusion formed of a thin-walled, resilient tubing, (ii) torque-transmitting means for transmitting torque along said catheter proximal portion, (iii) axially incompressible means for precluding both compression and kinking of said catheter proximal portion, (iv) a large aperture extending through said catheter proximal portion, (v) at least a pair of relatively small flexible shafts, each said small shaft extending through said large aperture and defining a relatively small lumen, (vi) a coaxial cable disposed in and extending through said large aperture, and (vii) a pair of steering wires, each of said steering wires extending through a respective one of said small lumens, and having a proximal end and exiting a proximal end of said respective small lumen and entering said handle; and (b) said proximal portion of said catheter including:

(i) a solid extrusion extension formed of resilient material for biasing said catheter distal portion to its home orientation and resisting kinking of said catheter distal portion, (ii) a large, central lumen through said catheter distal portion defined by said extrusion extension, (iii) at least a pair of relatively small, off-center lumen extensions through said catheter distal portion defined by said extrusion extension, (iv) a coaxial cable extension extending through said large lumen, (v) a pair of steering wire extensions, said steering wire extensions extending through a respective one of said small lumen extensions and having a distal end attached to said cable extension adjacent a distal end thereof; and (vi) axially incompressible means for defining a flex plane intermediate said pair of steering wire extensions and enabling said steering wire extensions to bend said distal end to either side of said flex plane and;

(C) controller means, disposed in and actuatable from said handle, for placing tension on one of said steering wires while relaxing tension on the other of said steering wires, thereby to bend said distal end of said coaxial cable toward said tensed one of said steering wires.

18. The assembly of claim 17 wherein said flex plane is intermediate said small lumen extensions and said steering wire extensions therein and enables said steering wire extensions to bend said large lumen and said coaxial cable extension therein to either side of said flex plane.

19. The assembly of claim 17 wherein said incompressible means includes a spaced parallel pair of axially incompressible rods.

20. The assembly of claim 19 wherein said axially incompressible rods are circular in cross section.

21. The assembly of claim 19 wherein said incompressible rods are rectangular in cross section.

22. The assembly of claim 17 wherein said incompressible means is a single incompressible rod of rectangular cross-section defining said flex plane.

* * * * *